United States Patent [19] [11] 4,212,738
Henne [45] Jul. 15, 1980

[54] ARTIFICIAL KIDNEY

[75] Inventor: Werner Henne, Wuppertal, Fed. Rep. of Germany

[73] Assignee: Akzo N.V., Arnhem, Netherlands

[21] Appl. No.: 889,401

[22] Filed: Mar. 23, 1978

[30] Foreign Application Priority Data

Mar. 28, 1977 [DE] Fed. Rep. of Germany ....... 2713603
Sep. 17, 1977 [DE] Fed. Rep. of Germany ....... 2741888

[51] Int. Cl.$^2$ .................... B01D 31/00; A61M 1/03
[52] U.S. Cl. ............................ 210/94; 128/214 R; 210/321 B
[58] Field of Search ............... 210/22, 321 B, 321 A, 210/94; 128/214 R, 214 B, 44 E

[56] References Cited

U.S. PATENT DOCUMENTS

| 3,388,803 | 6/1968 | Scott | 210/321 |
|---|---|---|---|
| 3,536,611 | 10/1970 | Defilippi et al. | 210/22 |
| 3,608,729 | 9/1971 | Haselden | 210/321 B |
| 3,864,259 | 2/1975 | Newhart | 210/321 B X |
| 4,000,072 | 12/1976 | Sato et al. | 210/321 B X |

Primary Examiner—Frank A. Spear, Jr.
Attorney, Agent, or Firm—John H. Shurtleff

[57] ABSTRACT

A flexible artificial kidney, capable of being worn directly on the body of the patient, and characterized by a flexible hollow retentate chamber of about 3 to 50 cm$^3$ in volume surrounded by a jacketed flexible dialysate chamber of about 300 to 5,000 cm$^3$ in volume, preferably such that the dialysate chamber is at least about 100 times larger than the retentate chamber. Blood inlet and outlet lines to and from the retentate chamber are passed in fluid tight relationship through the jacketed wall of the dialysate chamber which in turn has a closable opening for filling and discharging the dialysate liquid. This artificial kidney is especially effective when adsorbent materials are added to the liquid in the dialysate chamber.

17 Claims, 10 Drawing Figures

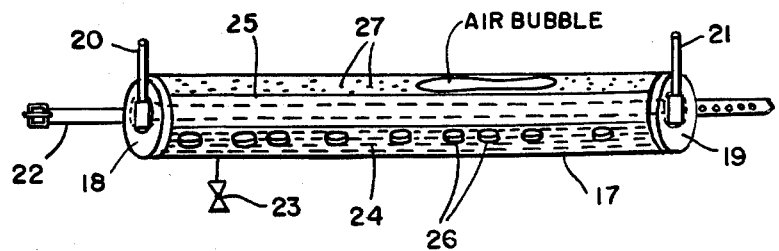
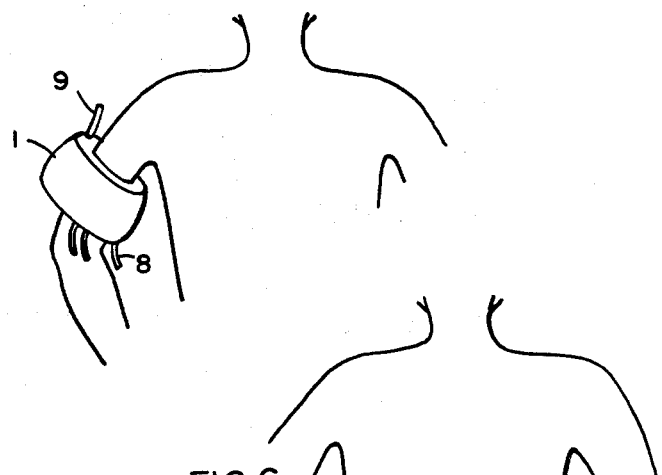
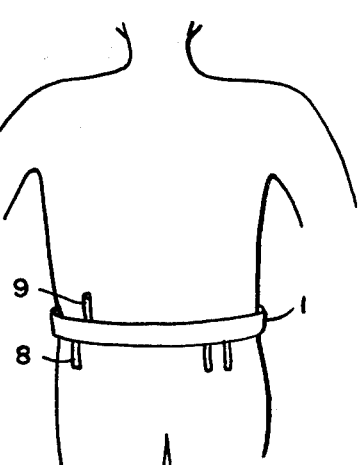
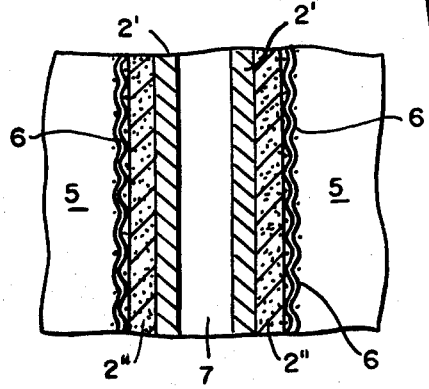
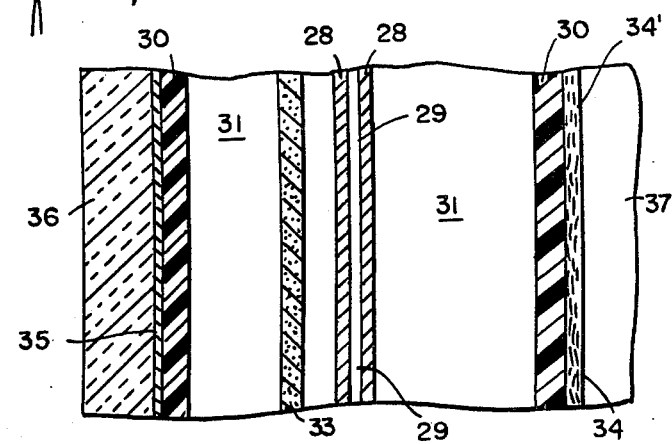

ARTIFICIAL KIDNEY

This invention relates to an artificial kidney which has a hollow retentate chamber for the passage of blood as formed by a dialysis membrane and, on the other side of the dialysis membrane, a hollow dialysate chamber is arranged with suitable connections for conveying the blood and filling or emptying the dialysate chamber. More particularly, this invention is directed to a portable artificial kidney which can be worn by the patient directly on his own body.

In the usual treatment of patients having an acute or chronic kidney disfunction, or after a nephron removal, other than using a kidney transplant, it has been a primary practice to connect the patient either at home or in a clinic to a central dialyzer to provide intermittent dialysis treatment on an artificial kidney. This type of treatment using various kinds of monitors and dialyzers compels the patient to be brought to the location of the artificial kidney to be connected for many hours per week, as a rule three days per week for six hours per day, as the patient lies in bed or on a reclining couch. It is therefore understandable that attempts have been made to reduce these treatment periods by ever more intensive treatment methods and apparatus.

These trends toward more effective treatments are not without negative effects on the patients, however, especially when in the discharge of metabolism products, it departs even further from the function of a normal person's healthy kidney which operates continuously so as to constantly eliminate small amounts of metabolites into the urinary bladder. Thus, after a highly effective 6-hour treatment, the metabolites in the patient's bloodstream are reduced far below normal concentrates. On the other hand, just before this 6-hour treatment, the concentration of metabolites in the bloodstream is much higher than normal.

Other methods have been tried for improving the patient's state of health, for example, by increasing the number of dialysis treatments to a daily 2-hour period. However, this procedure even further limits the patient's freedom of movement, and causes a complication due to the more frequent connection and disconnection of the apparatus, something which results in higher blood losses.

Portable artificial kidneys (Kolff) have been developed which depend upon a miniaturization of the equipment in the monitoring system, e.g. blood pump, dialysate pump, thermostat, regulator, temperature and pressure measuring devices, etc., which require adsorption equipment for the dialysate circulation and are therefore still relatively extensive, so that the artificial kidney must be carried on an abodominal casing or in a back pack. Also, this portable apparatus depends on the principle of intermittent dialysis and offers very little freedom of movement for the patient.

With these known artificial kidneys including the portable type used for intermittent dialysis, one starts from the premises that the dialysis should take place on a membrane surface which is as large as possible, for example 2 to 3 m², thereby necessarily requiring a correspondingly high volume of blood, and that the exchange of material is at its highest efficiency when the volume of the dialysate within the artificial kidney is as small as possible. In general, the selected ratio of the blood volume to the dialysate volume is approximately 1:1. As long as a patient is to be connected to a dialyzer for the quickest possible dialysis, these various conditions must be fulfilled.

It is an object of the present invention to provide a portable artificial kidney which will operate continuously, which will eliminate the need for auxiliary apparatus such as pumps, thermostats, valves and regulators and which can be carried continuously by patients without any significant difficulty while remaining connected with the blood circulation over a long period of time.

These and other objects and advantages are achieved, according to the present invention by means of an artificial kidney which is characterized by the fact that the total volume of the hollow chamber formed by at least one dialysis membrane to conduct the blood is about 3 to 50 cm³ while the volume of the dialysate chamber is about 300 to 5,000 cm³, and also that the dialysate chamber is enclosed by a casing or jacket which is conformed to or conformable with a part of the human body on which the portable device is carried. Both the dialysate chamber and the retentate chamber for the blood should be sufficiently flexible so that the portable artificial kidney can be easily conformed to a part of the body, e.g. the arm, leg, waist, chest or the like. The dialysate chamber has at least one closable opening or valved port for filling or discharging dialysate liquid. The retentate chamber has blood inlet and outlet lines passed through the outer jacket in fluid-tight relationship for circulation of blood from the patient through the device and back to the patient.

The total volume of the retentate chamber for passage of the blood through said at least one dialysis membrane is preferably about 5 to 25 cm³ with the volume of the dialysate chamber on the other side of the membrane preferably being about 500 to 2500 cm³.

The volume of the dialysate chamber is thus considerably larger than the volume of the retentate chamber, e.g. about 40 times larger or more, preferably at least 70 times larger and especially at least 100 times larger.

Various embodiments of the invention are illustrated by the accompanying drawings in which:

FIG. 3 is a side elevational view, in partly schematic form, to illustrate a hollow fiber dialyzer constructed according to the invention with an outer flexible tubular casing forming the dialysate chamber around an inner hollow fiber bundle as the dialysis membrane;

FIGS. 4, 5 and 6 are schematic illustrations of the manner in which the portable dialyzer can be worn around the arm, leg or waist; respectively;

FIG. 6a is a highly enlarged partial cross-sectional view of a flat tubular membrane such as that used in the device of FIGS. 1 and 2; and FIG. 6b is another enlarged partial cross-sectional view of the various layers used in a preferred construction of the artificial kidney of the invention.

Figure 1:
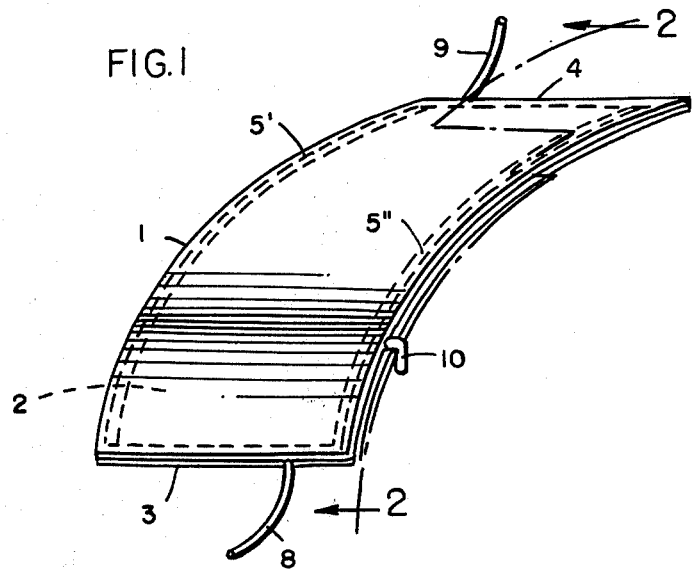
FIG. 1 is a perspective view of a relatively flat, portage, artificial kidney according to the invention which is quite flexible so as to be wrapped around a part of the body.
Figure 2:
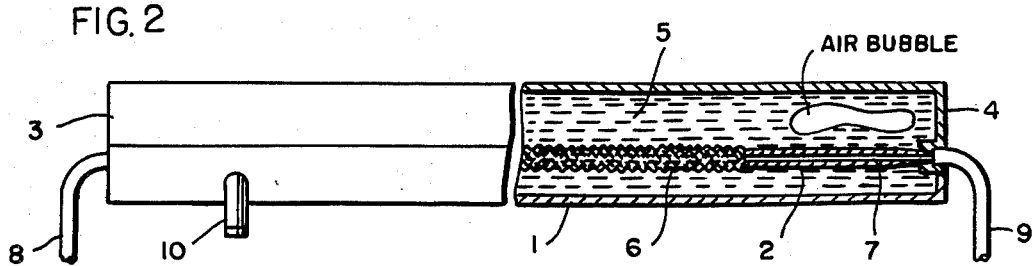
FIG. 2 is a partial sectional view taken along the line 2—2 of FIG. 1 to show a partial cross-section of both the outer jacket and the inner dialysis membrane.

Referring first to FIGS. 1 and 2 of the drawings, the relatively lightweight, flexible and portable artificial kidney is generally constructed as an outer jacket 1 surrounding an inner flat tubular dialysis membrane 2 which is fastened at either end 3 and 4 of the jacket 1 so as to be suspended within the hollow dialysate space 5. The membrane 2 is spaced inwardly from each longitudinal side of the jacket 1 to permit circulation of the dialysate through the spaces 5' and 5". A fine mesh plastic netting 6 is preferably applied around the membrane 2 for support and to hold it more firmly in place between the ends of the jacket 2. Blood passes through the inner hollow chamber 7, being introduced through inlet line 8 and discharged at outlet line 9. The hollow dialysate chamber 5 is filled or emptied through at least one valved or closable pipe 10. It will be understood that separate pipes or conduits can be provided for the purpose of filling and emptying the dialysate chamber.

Figure 2A:
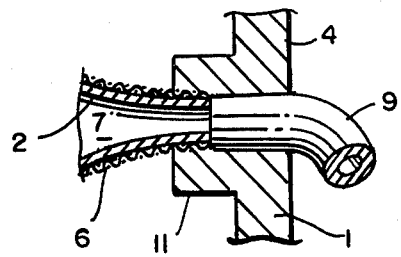
FIG. 2a is a partial sectional view to illustrate one fluid tight connection of a blood inlet or outlet line connected to the inner dialysis membrane through the outer jacket.
Figure 2B:
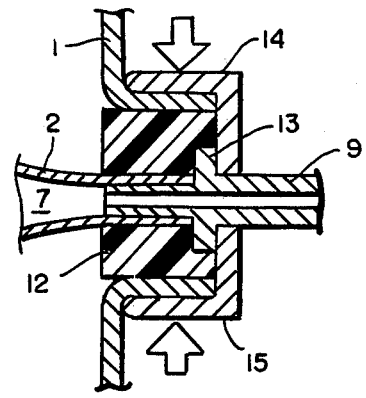
FIG. 2b is a partial sectional view similar to FIG. 2a to illustrate another fluid tight connection of the blood inlet or outlet line.

The blood feed and discharge lines 8 and 9 must be tightly sealed so as to avoid any leakage of fluid where they pass through the jacket 1. As indicated in FIG. 2a, the line 9 can be permanently sealed by a suitable adhesive or bonding agent in the end wall 4 of the jacket 1, the dialysis membrane also being tightly sealed along an inner projecting seam 11 of the jacket. In FIG. 2b, a fluid-tight seal is obtained even though the line 9 can be removably inserted for liquid connection with the interior retentable chamber 7 of the dialysis membrane 2 (netting omitted). The resilient and preferably elastomeric mounting member 12 has a hollow bore to receive the inner projecting tip of the line 9, an annular recess receiving the flange 13 of line 9. A portion of the end wall of jacket 1 is flared outwardly to lie along the mounting member 12 and pressed or clamped tightly in place by the upper and lower clamps 14 and 15, respectively, the clamping pressure being indicated by the arrows as supplied by a spring clamp, a screw clamp or the like.

The portable artificial kidney shown in FIG. 3 represents a preferred embodiment of the invention having a number of special features. The outer casing or jacket 17 in this case is a transparent, flexible polymer material in the form of an elongated tube, bowed slightly inwardly at the middle as illustrated, with two end caps 18 and 19 carrying the blood inlet and outlet lines 20 and 21, respectively. This tube 17 is bowed in the opposite direction when worn by the patient, e.g. around the waist, and can be fastened in place by means of the belt 22. The tube jacket 17 can also be transparent only in part, e.g. around one-half or three-quarters of its circumference, and snaps, draw strings, clamps, or other fastening means can be used to mount the jacket on its back side to the belt 22.

At least one valved line 23 is used again to fill and empty the dialysate chamber 24 formed between the jacket 27 and an inner tubular bundle of hollow fibers or filaments 25. Each hollow fiber or filament serves as an individual dialysis membrane in the nature of a capillary membrane, all of the filaments extending between and in liquid connection with the inlet 20 and outlet 21 at either end of the flexible dialyzer. Such hollow filaments are conventional, preferably of a cuprammonium regenerated cellulose, and provide a very low volume retentate zone compared to the dialysate zone 24.

Adsorbent materials are visible within the dialysate, either as solid tablets 26 and/or as suspended particles 27.

FIGS. 4, 5 and 6 indicate various ways in which the jacketed dialyzer 1 can be worn on the patient's body, e.g. using the tubular membrane of FIGS. 1 and 2.

In FIG. 6a, the adsorbent particles such as active carbon are contained in an outer layer 2' of a tubular dialysis membrane, the inner layer 2" being formed of pure cellulose as obtained by regeneration from a cuprammonium solution. As in FIG. 2, the membrane can be supported by a fabric or plastic netting material 6 as the blood passes through the central hollow chamber 7.

In FIG. 6b, a number of other preferred variations are shown in a relatively flat tubular membrane dialyzer, the two-sided dialysis membrane 28 defining the hollow retentate chamber 29 for the passage of blood and the surrounding two-sided silicone rubber jacket 30 defining the enclosed dialysate chamber 31. In this case, an additional cellulosic layer 32 is provided in the dialysate space, this extra layer 33 containing particles of an adsorbent as indicated. A fabric laminate is bonded to the outer surface of the silicone rubber wall layers of the jacket, e.g. preferably with one laminate layer 34 containing small fibers or particles 34' of a heat-conducting metallic additive, thereby providing good heat transfer from the body of the patient 37 to the liquid in the dialysate chamber 31. An outer fabric laminate 35 may be optionally used as a means of firmly adhering an insulation layer 36 around those surfaces of the jacket which remain away from contact with the patient. This combination of features is of particular value as explained in further detail hereinafter.

In the operation of the portable dialyzer of the invention, the washing of the membrane layer or layers for taking up the metabolites occurs through movement of the body member which carries the artificial kidney as illustrated herein. With each natural movement of the body, the liquid flows along the membrane and takes up the metabolites being diffused throughout, especially when the dialysate chamber is not completely filled but instead is filled only up to about 4/5 or 9/10 with the dialysate liquid.

This partial filling of the dialysate chamber is also important for the reason that room is retained for the ultrafiltered water. A blood pressure between about 80 and 130 mm Hg in the blood circulation of the patient provides for the transport of the blood through the hollow retentate chamber formed by the dialysis membrane without using any additional pumps for this blood conveyance. Also, this normal blood pressure also provides the necessary dewatering. The ultrafiltered water must be taken up from the dialysate chamber. The artificial kidney of the invention requires no special pumps, either for the blood conveyance or for the movement of the dialysate.

When by means of the continuous dialysis, similar to the glomerular filtrate of the natural kidney, both the dialysate volume increases and also its metabolite concentration increases, such that the concentration differential ($\Delta c$) between the blood and the dialysate is lowered, the patient is required only at regular preset intervals of time, e.g. hourly, every 2 hours or every 3 hours, to draw off the dialysate and replace it with a fresh supply from a previously made up bag or cannister of the standard solution. The blood circulation of the patient remains undisturbed. Moreover, it is possible to control the amount of dialysate by its volume.

The artificial kidney of the invention is connected to the patient in the conventional manner, preferably over the shortest path by means of polyurethane tubes or even with suitable vascular replacement systems which are connected to the veins and/or arteries of the patient, commonly referred to as arteriovenous tubing or more simply A-V tubing or blood lines. The point of connection must be only sufficient for installing a clamp in exchanging the artificial kidney.

The hollow space formed by the dialysis membrane, i.e. the retentate chamber, must be filled air-free with a physiological brine solution (sodium chloride solution) before the artificial kidney is connected. The small hollow space volume which represents the total blood volume of the artificial kidney after its connection makes it possible for the slight filling capacity of the hollow space to be supplied with physiological brine solution without losses in the connection onto the circulation of the patient.

In general, a regular interval or cycle of about 2 to 3 hours will be observed for emptying the dialysate chamber and refilling it with make-up dialysate. The relatively high dialysate volume which can be provided by the artificial kidney of the invention, opens up the possibility of also utilizing the night hours for dialysis.

In the preferred form of the invention, the jacket or housing has those surfaces which come in contact with the patient's body made of a material of good thermal conductivity while the remaining surfaces are preferably protected by a good insulating material. For example, to obtain good thermal conductivity from the body, it is possible to use a plastic or polymer structural material which contains a filler capable of increasing thermal conductivity, for example, a metal powder, metal fibers or the like. The heat insulating can be obtained by a covering of wadding, e.g. cotton, glass wool or similar voluminous, porous materials. Through these means, the temperature of the dialysate is kept practically at body temperature. Thermostats, thought to be indispensible with artificial kidneys, can be avoided with the portable artificial kidney of the present invention.

The jacket or housing of the invention is preferably a flexible material which, within the scope of this invention, is a material sufficiently pliable or bendable that it will press up against the surface to which it is applied but at the same time will not be deformed by the weight of the dialysate within the jacket such that the enclosed volume will be substantially altered. Because the dialysis membranes are also flexible, the entire artificial kidney is very easily applied around various parts of the body and will easily conform to surface irregularities so as to maintain close contact with the body along one surface.

Through the use of a flexible jacket, the dialysate which does not completely fill the empty volume of the jacket is agitated very strongly by the normal bodily movement of the patient so that at the outer walls of the dialysis membrane the boundary layer of the dialysate is continually renewed without requiring pumps or other driven mechanical means. The flexible jacket is therefore an essential feature of the invention in being conformable or fitted to a bodily member of the patient but also retaining a substantially constant volume in the dialysate chamber when filled about 4/5 to 9/10 of its capacity.

One well-suited flexible material for the jacket is a silicone rubber. In special circumstances, a jacket made of polyurethane has given useful results. Other plastic materials may also be used or even composite structures such as laminates or impregnated fabrics or felts may be used to achieve especially desirable properties.

Many patients, especially if they must carry the artificial kidney of the invention over an extended period of time, exhibit troublesome skin irritations or severe discomfort with certain flexible materials. Therefore, it is an especially preferred embodiment of the invention to provide a flexible jacket comprising a fabric laminate. In this case, the fabric side is carried against the skin while the lamination, e.g. a plastic or polymeric material, is turned toward the side receiving the dialysate liquid. Suitable laminating materials include elastomers and other polymers or plastic foils while any suitable textile material can be used for the fabric, preferably a cotton and plastic foil laminate.

Although flexible jackets are especially preferred to provide the portable artificial kidneys of the invention, it is also possible to select any conventional material generally adapted for use in dialyzers. Among such materials are polycarbonates, polyurethanes, polyolefins, polyvinyl chloride, polyamides, polyesters and polyacrylates.

A further preferred embodiment of the invention consists in the use of a jacket composed at least partly of a transparent material as suggested by FIG. 3. By using a transparent material, the state or condition of the artificial kidney can be readily observed from outside. The above-noted polymers can be readily obtained in useful transparent form. For most purposes, however, moldable plastics are preferred.

In order to exchange the dialysis membrane, the artificial kidney can be made such that the jacket or casing is divisibly constructed, i.e. so that it may be partly disassembled as indicated in FIG. 2b. Thus, the dialysis membrane as well as the jacket can be embedded or clamped in place such that the feed and outlet lines through the jacket are placed in fluid-tight connection with the dialysis membrane while passing through the end walls of the jacket.

The demand for a small blood volume with little disturbance of the flow is best fulfilled by using a hollow fiber dialysis membrane. In general, these may be in the form of a single filament or in the form of a bundle of filaments which are embedded at the ends in a molded plastic member such as the discs appearing at either end of the jacket in FIG. 3. Such hollow fibers or filaments can be produced from polycarbonates, polypeptides, polyurethanes, polysulfones, acrylic polymers and aromatic polyamides.

It is especially preferred to use membranes composed of a regenerated cellulose because of their good dialysis properties. Above all, membranes of cellulose regenerated from cuprammonium solutions have been found to be especially suitable as membranes for the artificial kidneys of the invention.

When using hollow fibers or filaments, the inner diameter of each fiber preferably amounts to about 100 to 1,000 $\mu$m with a wall thickness of about 10 to 30 $\mu$m, the fibers being collected together into a bundle having a total surface area of less than 0.3 $m^2$.

One great advantage that is made possible by the artificial kidney of the present invention resides in the fact that blood clotting problems are substantially reduced due to very small amount of foreign surfaces. If needed, heparin can be introduced into the dialysate. The metabolite concentration in the plasma of the patient undergoes only slight variations, just as in a normal healthy kidney, so that detrimental pathological symptoms do not arise, at least to the extent found with the use of intermittent dialysis where there are wide variations of concentration of substances in the blood serum. It is these wide variations which can cause kidney patients to be sensitive to the middle molecules and which lead to the neuropathic states previously experienced in intermittent dialysis.

In using the artificial kidney of this invention, the kidney patient needs to visit his doctor only once per week in order to have a new dialyzer attached and the necessary dialysis make-up bag or cannister prescribed. The composition of the dialysate can be individually adapted to the specific form of the illness and, as may be needed, various medicines and/or enzymes can be added to the dialysate, e.g. urease to promote the decomposition of urea by hydrolysis.

The artificial kidney of the invention can be made up partly or completely of components of various ready-to-wear forms of the dialyzer, e.g. as arm bands, leg bands, pants or trousers, vests, chest bags, abdominal girdles, and the like. They can be worn at any suitable body position which is extracorporeal and conformed to the body, preferably so as to be connected with the shortest possible vascular connection. It will be understood, of course, that the jacket of the dialyzer may contain fluid connections or reinforcing elements, e.g. in order to fix the dialysis membrane in a specific position.

It has further been proven that the artificial kidney is still further improved if it contains at least one adsorbent outside of the retentate chamber in which the blood flows, e.g. as illustrated in FIGS. 3, 6a and 6b of the drawings. By using the adsorbents in this manner, it is possible to substantially increase the time interval at which the dialysate must be replaced, thereby providing the patient with a greater freedom of movement while at the same time increasing the effectiveness of the dialysis by raising the concentration differential ($\Delta C$).

The artificial kidney of the invention can be constructed such that at least one adsorbent layer is arranged in the dialysis membrane itself as in FIG. 6a. These special types of membranes are described in detail in the German Patent Applications identified as P 26 27 858.0 and P 27 05 734.7, corresponding to the earlier filed and copending U.S. Applications Ser. No. 808,924 and Ser. No. 809,486, the subject matter of these U.S. Applications being incorporated herein by reference as fully as if set forth in their entirety.

In a very simple manner, however, the artificial kidney of the present invention is very substantially improved by the simple expedient of adding the adsorbents directly to the dialysate. In this case, the adsorbents should be introduced in the form of granules, tablets, little rods or the like as illustrated in FIG. 3. These specific embodiments are distinguished by their simplicity because of the extreme ease of adding the adsorbents in this particulate or tablet form to the dialysate as compared to the incorporation of the adsorbent materials in one or more membrane layers.

Another favorable embodiment of the present artificial kidney resides in the use of a closed chamber formed by a dialysis membrane filled with adsorbent and arranged in the dialysate space or chamber, i.e. as illustrated by the additional membrane 33 in FIG. 6b which contains adsorbent particles and which is not used directly for hemodialysis by passing blood therethrough, but instead acts to adsorb metabolites which have first been taken up by the dialysate liquid and are only then separated from the dialysate and held by the adsorbent material in membrane 33. This additional membrane 33 may be constructed with a hollow central space as in the dialysis membrane 28 or it may also be solid with the adsorbent distributed therein.

As useful adsorbents for the artificial kidney of the invention, a wide selection may be made but preferably including active carbon, aluminum oxide, zircon oxide, zircon phosphate, silicic acid and/or silicates, all of which have good adsorbent properties.

It has been known to add on an adsorption unit in the circulation of the dialysate in those artificial kidneys which have been used by connecting them intermittently to the patient. In this case, however, a large amount of ultrafiltrate had to be decontaminated and reconveyed over a filter. The artificial kidney of the present invention avoids such problems while still providing a more effective dialysis treatment.

The advantages of the artificial kidney of this invention, aside from providing adsorbents outside of the retentate or blood passageways, resides in the very noticeable prolongation of time between changes of the dialysate. As a result, there is a large reduction in the cost of the dialysate due to its more economical use, and in addition the night hours are better used for the dialysis treatment. Such desirable results are achieved primarily because the metabolite concentration in the dialysate can be maintained so low over a long period of time that the full concentration differential between the circulating blood and the dialysate can be maintained over much longer periods of time. The ease of use and the avoidance of excessive apparatus and monitoring equipment are also significant advantages.

The functioning and effectiveness of the artificial kidney according to the invention are clearly illustrated by the following examples.

EXAMPLE 1

The dialyzer used consisted of a hollow filament bundle of 125 cellulose filaments obtained by regeneration from a cuprammonium solution, each filament having an inner diameter of 600 $\mu$m, a wall thickness of 15 $\mu$m and a length of 850 mm, apart from the embedding layers, mounted in a flexible casing having inside measurements of 85·10·2.6 cm$^3$=2,200 cm$^3$ filled with 2 liters of a physiological brine solution, i.e. a conventional sodium chloride solution required as the dialysate.

The total hollow space volume of the hollow filament bundle in the dialyzer amounted to 30 cm$^3$, and a urea solution of 1,000 mg/l was pumped through the hollow filaments with a throughput of 40 ml/min. The internal pressure of the hollow filaments was maintained at 100 mm Hg by means of a clamp on the outlet or discharge line of the hollow filament bundle. The dialyzer was steadily rocked back and forth at a rate of 3 oscillations per minute. After a time lapse of ½, 1, 1½ and 2 hours, respectively, a small test sample of the dialysate was withdrawn in each case. Analysis of each sample gave the following urea concentrations:

| Time Lapse | Urea Concentration |
|---|---|
| After ½ hour | 322 mg/l |
| After 1 hour | 536 mg/l |
| After 1½ hours | 685 mg/l |
| After 2 hours | 786 mg/l |

After this 2 hour operation of the dialyzer, the dialysate was drained off and the casing filled with 2 liters of fresh brine solution. After another two hours of operation, the urea concentration of the dialysate increased to 780 mg/l. In this specified manner, it was thus possible on the average to separate 1.566 g of urea every 2 hours. The amount of liquid in the dialysate casing was measured when emptied therefrom and amounted in each case to about 2,060±2 ml.

EXAMPLE 2

The dialyzer used in this example consisted of a hollow filament bundle of 350 cellulose filaments obtained by regeneration from a cuprammonium solution, each filament having an inner diameter of 300 μm, a wall thickness of 19 μm and a length of 300 mm (hollow space volume = 7.4 cm$^3$), measured between the embedding layers, and a casing having interior measurements of 30·10·3.6 cm$^3$ = 1.1 liters, filled with physiological brine solution. A urea solution of 100 mg/l was pumped through the hollow filaments with a throughput of 20 ml/min, and the dialyzer was rocked at a frequency of 3 oscillations per minute. The internal pressure in the filamentary hollow space was maintained at 100 mg Hg excess pressure. After ½ hour and 1 hour, a small test sample was withdrawn in each case with the following results:

| Time Lapse | Urea Concentration |
|---|---|
| After ½ hour | 315 mg/l |
| After 1 hour | 530 mg/l |

The dialysate was then replaced by a fresh solution, and the dialysis was repeated for 1 hour with practically the same results.

EXAMPLE 3

A cubical container made of a transparent polycarbonate was constructed with a length of 33 cm, a width of 17 cm and a height of 2 cm, formed as two halves, i.e. a base portion of 1 cm in height and a cover portion also of 1 cm in height. This container was used as the casing or housing for the artificial kidney of the invention. A dialyzer of these dimensions can be worn on the chest, the waist or the back of a person, where it can be more closely conformed to the shape of the body by curving it around the body. At the upper edge of the base portion of the casing, there was positioned a tubular dialysis membrane composed of cellulose, which had been regenerated from a cuprammonium solution, to provide a flat tubular retentate chamber of 15 cm in width and 33 cm in length, the interior volume of the retentate chamber hollow space being 25 cm$^3$. This flat tubular membrane was further enclosed on both sides by a plastic netting of the same length as the membrane but with a width of 16 cm, the netting being formed of five strands or crosspieces arranged at intervals of 0.05 cm so as to centrally fix the tubular membrane in place. This construction reduced the cost of the end walls. Feed and outlet lines for the blood were thus brought in from outside by means of a slot facing the flat tubular inner chamber and a round opening for the tubular connection projecting to the outside.

In place of the tubular dialysis membrane, it is also possible to use two flat sheet membranes adhered along their longitudinal edges, or one may also use a similar flat shaped hollow filament bundle.

The cover portion of the cubical container was clamped in place to form a fluid tight enclosure with the tubular membrane suspended about halfway between the top and bottom but with liquid circulation possible through the netting along the longitudinal edges of the membrane.

The dialyzer was then filled with 1 liter of sodium chloride solution, and a creatinine solution of a concentration of 100 mg/l was passed as a layer through the inner hollow chamber formed by the membrane in the sodium chloride solution, the rate of throughput being 20 ml/min. The dialyzer was vertically agitated while standing on end over a time period of one hour. After this one hour, 53 mg of creatinine was separated from the artificial blood circulation.

EXAMPLE 4

An artificial kidney well suited for being carried on the leg above the knee or on the arm above the elbow consists of a two-part casing or jacket housing. Around the leg with a circumference of 40 cm, for example, a collar of a silicone rubber having good thermal conductivity was buckled in place. Along the circumference of this collar, there are contained at intervals of 10 cm a number of L-straps of silicone rubber into which there were pressed the corresponding counterparts of the cover portion of the artificial kidney so as to remain fluid tight. The approximately 35 cm long cover portion consists of a flexible polyurethane and has about 4 cm high side members so as to enclose a dialysate volume of about 1.4 liters. Into the end walls of the cover portion, a bundle of cellulosic hollow filaments, consisting of cellulose regenerated from a cuprammonium solution, was enclosed so as to be fluid tight except for nipples or short little tubular pipes projecting outwardly for the blood feed and discharge lines. The hollow filaments have an inner diameter of 600 μm and a wall thickness of 10 μm. The membrane surface amounted to 0.1 m$^2$, and the hollow space volume of the dialysis membrane was about 15 cm$^3$. The cover portion is loosely opened for its insertion, in order to lay it around the collar and press it firmly into the angular guide straps.

EXAMPLE 5

There was prepared a hollow filament dialyzer of cellulose hollow filaments with a membrane thickness of 11 μm and an inside diameter of 200 μm, so as to provide a free filament length of 11 cm with an effective membrane surface of 0.1 m$^2$ and a hollow space volume of 4.5 cm$^3$, all installed in a housing or casing having a liquid capacity of 1.1 liters.

In this dialyzer, there was tested a simulated blood having the following composition:

| Substance | Concentration |
|---|---|
| Urea | 1,310 mg/l |
| Creatinine | 155 mg/l |
| Uric acid | 58 mg/l |
| Phosphorus (a mixture of $Na_2HPO_4$ + $NaH_2PO_4$ in a ratio of 4:1) | 50 mg/l |
| Vitamin B12 | 20 mg/l | all in a physiological sodium chloride solution.

This solution, which represents a simulated blood, was warmed to 37° C. and flowed through the blood compartment of the dialyzer, i.e. through the hollow filaments, after the dialysate side had been filled with physiological brine solution as the dialysate, also at a temperature of 37° C. In order to initiate a bodily movement of the dialyzer, it was tipped once every 15 seconds through 90° from the vertical with respect to its filament bundle axis, thereby constantly agitating the dialysate.

Two different series of tests were carried out:
(a) without adsorbents in the dialysate; and
(b) with 5 g active carbon in tablet form and 5 g $Al_2O_3$ in powder form distributed in the dialysate.

The apparatus was operated so as to provide a pressure differential between the blood side and the dialysate side of less than 10 mm Hg, such that the ultrafiltration had no measurable influence.

During a two-hour dialysis run, a sample of the simulated blood stream was withdrawn every ½-hour for analysis and calculation of the clearance and material transfer values, while the "blood-supply" was separated and the dialysate was examined at the end of the dialysis. Since the concentration of the dissolved substances could not be used in those runs with adsorbents in the dialysate for the determination of material transfer, the amounts of substances separated from the simulated blood were calculated in all cases from the clearance values, i.e. from the inlet and outlet concentrations.

The results of the two series of tests are set forth in the next following Table.

The elimination of the "blood poisons" is increased in all cases by use of an adsorptive material in the dialysate. The effect of adsorbents on urea is the least, while the effect on vitamin B12 is much higher, it being understood that vitamin B12 serves in this case only as a test substance for an assumed uremia poison having the same order of magnitude of molecular weight. In this molecular weight range, the elimination of the undesired substance is determined first of all by the membrane permeability. The increased separation of materials of up to as much as 58% can be utilized in order to reduce the frequency of changing the dialysate or for reducing the size of the dialyzer. Both of these possibilities are desirable from a medical viewpoint as well as being of greater value for the individual patient.

TABLE

| | Separation of dissolved substances from the simulated blood. | | | |
|---|---|---|---|---|
| | Amounts of substances separated | | | |
| | Dialysate changed hourly | | Diolysate changed every 2 hrs | |
| Substance | per hour (mg) | per day (mg) | per 2 hrs. (mg) | per day* (mg) |
| A. Urea- | | | | |
| 1. Without adsorbent | 785 | 15,700 | 1,015 | 10,150 |
| 2. With adsorbent | 825 | 16,500 | 1,096 | 10,960 |
| Relative increase | | +5% | | +8% |
| B. Creatinine- | | | | |
| 1. Without adsorbent | 82 | 1,640 | 121 | 1,210 |
| 2. With adsorbent | 102 | 2,040 | 172 | 1,720 |
| Relative increase | | +24% | | +42% |
| C. Uric acid- | | | | |
| 1. Without adsorbent | 29 | 580 | 44 | 440 |
| 2. With adsorbent | 35 | 700 | 63 | 630 |
| Relative increase | | +20% | | +43% |
| D. Phosphorus- | | | | |
| 1. Without adsorbent | 25 | 500 | 38 | 380 |
| 2. With adsorbent | 35 | 700 | 60 | 600 |
| Relative increase | | +40% | | +58% |
| E. Vitamin B12 | | | | |
| 1. Without adsorbent | 3.6 | 72 | 6.5 | 65 |
| 2. With adsorbent | 4.8 | 96 | 8.4 | 84 |
| Relative increase | | +33% | | +29% |

*The daily amounts were determined as 20 times the hourly amounts when using the hourly change of dialysate and as 10 times the 2-hour amounts when using the two hourly change of dialysate.

The invention is hereby claimed as follows:

1. A portable artificial kidney comprising a flexible hollow retentate chamber for the passage of blood formed by at least one dialysis membrane, and a flexible dialysate chamber formed by a jacket displaced outwardly and surrounding said at least one dialysis membrane, the volume of said retentate chamber being about 3 to 50 cm$^3$ and the volume of said dialysate chamber being about 300 to 5,000 cm$^3$ with the proviso that the volume of the dialysate chamber is at least about 40 times the volume of the retentate chamber, said dialysate chamber having at least one closable opening for filling or discharging a dialysate liquid and said retentate chamber having blood feed and outlet lines passed through said jacket in fluid-tight relationship, the combined dialysate and retentate chambers being sufficiently flexible to be conformed to a part of the human body and said dialysate chamber being only partially filled with dialysate liquid to provide a gas bubble which is sufficiently large to ensure liquid flow along the dialysis membrane with each natural movement of the body.

2. A portable, artificial kidney as claimed in claim 1 wherein the retentate chamber has a volume of 5 to 25 cm$^3$ and the dialysate chamber has a volume of 500 to 2500 cm$^3$.

3. A portable, artificial kidney as claimed in claim 1 wherein the volume of the dialysate chamber is at least 100 times the volume of the retentate chamber.

4. A portable, artificial kidney as claimed in claim 1 wherein the jacket surface contacting the human body is made of a material having good heat conductivity and the remaining jacket surface is made of a heat-insulating material.

5. A portable, artificial kidney as claimed in claim 1 wherein the jacket consists essentially of a flexible, elastomeric polymer material.

6. A portable, artificial kidney as claimed in claim 1 wherein the jacket consists at least partly of a transparent flexible polymer material.

7. A portable, artificial kidney as claimed in claim 1 wherein the jacket consists at least partly of a silicone rubber.

8. A portable, artificial kidney as claimed in claim 1 wherein the jacket consists at least partly of a polycarbonate.

9. A portable, artificial kidney as claimed in claim 1 wherein the jacket consists at least partly of a polyurethane.

10. A portable, artificial kidney as claimed in claim 1 wherein said jacket comprises a fabric laminate.

11. A portable, artificial kidney as claimed in claim 1 wherein the retentate chamber for the passage of blood is formed by a bundle of hollow filaments as the dialysis membrane.

12. A portable, artificial kidney as claimed in claim 1 wherein the dialysis membrane consists of cellulose which has been regenerated from a cuprammonium solution.

13. A portable, artificial kidney as claimed in claim 1 wherein at least one adsorbent material is arranged outside of the retentate chamber for contact with the dialysate liquid.

14. A portable, artificial kidney as claimed in claim 13 wherein at least one layer containing an adsorbent is arranged in the dialysis membrane.

15. A portable, artificial kidney as claimed in claim 13 wherein at least one adsorbent is contained in the dialysate.

16. A portable, artificial kidney as claimed in claim 15 wherein the adsorbent is arranged as a granulate, tablet or briquette in the dialysate.

17. A portable, artificial kidney as claimed in claim 13 wherein a closed chamber formed by a dialysis membrane is filled with adsorbent material and is arranged within the dialysate chamber.

* * * * *